United States Patent [19]

Hoppstock

[11] 4,002,696
[45] Jan. 11, 1977

[54] OXIDATIVE DEHYDROGENATION OF OLEFINS OVER A HIGH ACTIVITY COBALT-MOLYBDATE CATALYST

[75] Inventor: Frederic H. Hoppstock, Massillon, Ohio

[73] Assignee: The Goodyear Tire & Rubber Company, Akron, Ohio

[22] Filed: June 30, 1975

[21] Appl. No.: 591,264

[52] U.S. Cl. .................. 260/669 R; 260/680 E
[51] Int. Cl.² .................. C07C 15/10; C07C 11/12
[58] Field of Search ....... 260/680 R, 680 E, 668 D, 260/669 R, 680 D; 252/470

[56] References Cited

UNITED STATES PATENTS

| | | | |
|---|---|---|---|
| 3,159,688 | 12/1964 | Jennings et al. | 260/680 E |
| 3,179,706 | 4/1965 | Lee | 260/669 R |
| 3,415,760 | 12/1968 | Hadley et al. | 252/470 |
| 3,574,729 | 4/1971 | Gasson | 252/470 |
| 3,692,860 | 9/1972 | Boutry et al. | 260/680 R |
| 3,843,555 | 10/1974 | Erpenbach et al. | 252/470 |
| 3,894,055 | 7/1975 | Farha et al. | 260/680 E |
| 3,917,736 | 11/1975 | Frech et al. | 260/680 E |

*Primary Examiner*—Oscar R. Vertiz
*Assistant Examiner*—Brian E. Hearn
*Attorney, Agent, or Firm*—F. W. Brunner; J. Y. Clowney

[57] ABSTRACT

There is disclosed a method comprising the oxidative dehydrogenation of at least one hydrocarbon selected from the group consisting of butene-1, butene-2, 2-methyl-1-butene, 2-methyl-2-butene, 3-methyl-1-butene, n-pentene, 2,3-dimethyl-1-butene, 2,3-dimethyl-2-butene, 2-methyl-1-pentene, 2-methyl-2-pentene, 4-methyl-2-pentene, 3-methyl-1-pentene, 3-methyl-2-pentene, 2-ethyl-1-butene, ethyl benzene and isopropyl benzene at oxidative dehydrogenation conditions while in the presence of a catalyst comprising cobalt-molybdate which has enhanced activity by being calcined at temperatures from 750°–1100° C for at least one hour prior to use in the oxydehydrogenation process.

10 Claims, No Drawings

OXIDATIVE DEHYDROGENATION OF OLEFINS OVER A HIGH ACTIVITY COBALT-MOLYBDATE CATALYST

This application is directed to an improved process of the oxidative dehydrogenation of hydrocarbons.

For instance, employing the process of this invention, butene-1 and/or butene-2 can be oxidatively dehydrogenated to butadiene, isoamylenes such as 2-methyl-1-butene, 2-methyl-2-butene and 3-methyl-1-butene to isoprene, n-pentenes to piperylene, 2,3-dimethyl-1- or 2-butenes to 2,3-dimethyl-1,3-butadiene, methyl pentenes such as 2-methyl-1-pentene, 2-methyl-2-pentene, 4-methyl-2-pentene, 3-methyl-1-pentene, 3-methyl-2-pentene and 2-ethyl-1-butene to various methyl pentadienes, ethyl benzene to styrene and isopropyl benzene to α-methyl styrene.

The invention provides an oxidative dehydrogenation process which reduces or eliminates endothermic heat requirements, permits continuous burn-off of carbon from the catalyst, permits longer catalyst life, provides higher per pass conversions and higher yields or selectivity to the desired products. Thus, the process of this invention is somewhat more advantageous than those of the prior art.

In U.S. Ser. No. 481,583, filed June 21, 1974, now U.S. Pat. No. 3,917,736, issued Nov. 4, 1976, there is disclosed a method for the preparation of 2,3-dimethyl-butadiene-1,3 comprising the oxidative dehydrogenation of 2,3-dimethyl-1-butene and/or 2,3-dimethyl-2-butene by contacting these hydrocarbons with a catalyst consisting of cobalt-molybdate or cobalt-molybdate treated with potassium hydroxide in amounts from about 0.5 to about 2 percent by weight of the cobalt-molybdate in the presence of an oxidant in an amount to provide oxygen/hydrocarbon mole ratio ranging from 0.5/1 to 5/1 at a temperature ranging from 350° C to 650° C and at an LHSV of from 0.5 to 10.

It has been discovered that if the catalyst comprising cobalt-molybdate or cobalt-molybdate treated with KOH in small amounts is calcined at temperatures between about 750° C and about 1100° C for at least one hour prior to use, the activity of the catalyst is greatly enhanced.

Therefore, accordingly, the invention is an improvement in the process of oxidative dehydrogenation of at least one hydrocarbon selected from the group consisting of butene-1, butene-2, 2-methyl-1-butene, 2-methyl-2-butene, 3-methyl-1-butene, n-pentene, 2,3-dimethyl-1-butene, 2,3-dimethyl-2-butene, 2-methyl-1-pentene, 2-methyl-2-pentene, 4-methyl-2-pentene, 3-methyl-1-pentene, 3-methyl-2-pentene, 2-ethyl-1-butene, ethyl benzene and isopropyl benzene to oxidative dehydrogenation conditions which in the presence of a catalyst consisting of cobalt-molybdate or cobalt-molybdate treated with potassium hydroxide in amounts from about 0.5 to about 2 percent by weight of the cobalt-molybdate in the presence of an oxidant in an amount to provide an oxygen/hydrocarbon mole ratio ranging from about 0.5/1 to about 5/1 at a temperature ranging from about 350° C to about 650° C and an LHSV of from about 0.5 to about 10, the improvement which comprises calcining the cobalt-molybdate or cobalt-molybdate treated with potassium hydroxide at temperatures between about 750° C and about 1100° C for at least one hour prior to use.

The oxidative dehydrogenation process of this invention can be conducted under fairly reasonable reaction conditions. For instance, the temperatures employed may vary from about 350° C to 650° C with 450° C to 600° C being more preferred.

In order to provide a better temperature control of the process and minimize excessive localized heating, it is usually desirable to employ a diluent, but a diluent is not absolutely required. Materials such as steam, nitrogen, methane, hydrogen, carbon dioxide or other diluents known to be stable under the reaction conditions may be employed. The diluent is employed at a diluent to hydrocarbon mole ratio from 1/1 to 20/1 with a more preferred range of 2/1 to 5/1.

While oxygen may be used as an oxidant, it is more economical and usually preferred to employ air as the oxidant. The oxidant mole ratio to the hydrocarbon feed (HC) in terms of $O_2$/HC should be between 0.1/1 and 10/1 with a more preferred range being 0.5/1 to 5/1 or 1/1 to 4/1.

The rate at which the hydrocarbon is passed through the reactor and is in contact with the catalyst is defined in terms of Liquid Hour Space Velocity (LHSV) and is defined as the volume of hydrocarbon as a liquid passed over or contacted with a given volume of the catalyst per hour. The LHSV employed in this invention should range from about 0.1 to about 100 with a more preferred LHSV of 0.5 to 10 being employed.

One interesting embodiment of this invention is the preparation of 2,3-dimethylbutadiene which comprises the oxidative dehydrogenation of 2,3-dimethyl-1-butene and/or 2,3-dimethyl-2-butene in the presence of cobalt-molybdate which has been calcined at temperatures between about 750° C and about 1100° C for at least one hour prior to being used, particularly mixtures of 2,3-dimethyl-1 and 2-butenes where the 2-olefin is in the range of about 65 to 80 mole percent.

The catalyst employed in this invention is cobalt-molybdate ($CoMoO_4$). The catalyst can be used in either its pure form such as pulverized $CoMoO_4$ or it can be employed as a physical mixture with or deposited on some support material normally employed in such hydrocarbon conversion processes. Examples of such support materials are alumina, silica-alumina, silica, silicon carbide, pumice, and the like.

The catalyst may be impregnated on a normal catalytic support material known in the art, for instance, alumina, silica, silica-alumina, magnesia, clays, pumice, titania, zirconias and the like. When the catalyst is impregnated on a support, the amount of $CoMoO_4$ should range from about 3 to 50 percent by weight, with about 10 to 30 percent being preferred and 12 to 16 being most preferred.

On the other hand, the catalyst of this invention may be coprecipitated from solutions containing various salts of cobalt and molybdenum and/or aluminum as hydroxides and then calcined to produce the catalyst $CoMoO_4$ impregnated on alumina.

Of course, it is usually conventional in a heterogeneous catalytic process such as that of this invention to employ continuous reaction systems with either fixed bed catalysts or fluidized bed catalysts. Therefore, it is usually preferred to employ the catalyst of this invention in a form which will not crush or be attrited easily. For that reason, it is usually more satisfactory to impregnate the catalyst from its salt onto a suitable rugged support in the form of pellets or fluidizable powder. It has been found in practice that the most suitable support is alumina. However, that is not to imply that other support materials such as silica, silica-alumina, magnesia, titania or zirconia are not acceptable or even crushed pumice and the like could be employed as the catalyst support.

The active catalyst itself, cobalt-molybdate, (CoMoO$_4$), at about 99.5 percent purity can be obtained commercially from The Ventron Corporation, Beverly, Mass, USA.

The catalyst may be treated with small amounts of a basic material such as potassium hydroxide or sodium hydroxide to moderate the acidic nature of the catalyst. This tends to prevent isomerization of, for instance, the feed of 2,3-dimethyl-2-butene to 2,3-dimethyl-1-butene. This treatment also prevents or retards the burning of the reactants and/or the products as such treatment lowers the amount of carbon dioxide found in the effluent. It also prevents the degradation into lower hydrocarbons or lights of the reactants and/or products. About 0.1 to about 10 percent by weight of the base, NaOH or KOH, may be employed for this moderation, with about 0.5 to about 2 percent being more preferred.

In order to obtain the higher activity of the catalyst employed in the process, the catalyst is required to be calcined at temperatures ranging from 750° C to 1100° C for at least one hour prior to use in the oxydehydrogenation process. The calcination of the catalyst whether it be in the form of pure cobalt-molybdate or cobalt-molybdate deposited on a support in amounts ranging from about 3 to 35 weight percent must be heated to at least 750° C for a period of at least one hour to obtain the improved activity. Highly active oxydehydrogenation catalysts comprising cobalt-molybdate have been calcined at temperatures between 750° C and 1100° C for periods of time from 1 hour up to 72 hours. Thus, the time required for the calcination is indicated to be at least one hour. This calcination requires no particular technique. The catalyst is placed in a suitable container and heated in an ordinary muffle furnace for the required period of time at the required temperature to effect the calcination.

The practice of this invention is further illustrated by reference to the following examples which are intended to be representative rather than restrictive of the scope of the invention. Unless otherwise indicated, all parts and percentages are by weight.

EXAMPLE I

In this example, run 1 is considered to be a comparative sample in which the final calcination temperature is only 600° C for 1 hour. The remaining runs 2 through 5 illustrate the practice of the invention. In Table 1, Col 2 is the temperature of the calcination of the catalyst for 1 hour, Col 3 is the conversion of the 2,3-dimethyl-2-butene, Col 4 is the selectivity to 2,3-dimethyl-butadiene-1,3 (DMBD), Col 5 is the mole ratio of steam to 2,3-dimethyl-2-butene, Column 6 is the mole ratio of oxidant to 2,3-dimethyl-2-butene in terms of O$_2$ and Col 7 is the total time on stream.

In each of these runs the oxydehydrogenation temperature was maintained at 525° C and the LHSV was 0.5. 2,3-Dimethyl-2-butene was the hydrocarbon subjected to the oxydehydrogenation. The catalyst consisted of 15 percent by weight of CoMoO$_4$ supported on alumina Al$_2$O$_3$ and had been modified by the addition of 1 percent KOH by weight prior to a one hour calcination, the calcination temperature being varied as listed.

The procedure employed was that the catalyst, about 6 cubic centimeters, was placed in a reactor of 0.43 inch internal diameter made from a stainless steel tube. The reactor was heated in a tubular furnace and the temperature was controlled by means of thermocouples placed at various locations along the reactor. The 2,3-dimethyl-2-butene feed and the diluent, water, were introduced as liquids using a syringe infusion pump. The air, which was the oxidant, was metered to the system. After the reaction had lined out the effluent from the reactor was analyzed directly using gas chromatographic techniques and used to calculate the conversion and selectivity.

TABLE 1

| Exp | Final Calcination Temp, °C | Conv | Select | H$_2$O/Feed | O$_2$/Feed | Total Run Time Mins |
|---|---|---|---|---|---|---|
| 1 | 600 | 42 | 83 | 2.8 | 1.0 | 120 |
| 2 | 750 | 56 | 76 | 3.4 | 1.4 | 120 |
| 3 | 800 | 61 | 76 | 3.4 | 1.3 | 120 |
| 4 | 940 | 64 | 82 | 4.0 | 1.3 | 155 |
| 5 | 1000 | 58 | 78 | 3.4 | 1.3 | 137 |

It can be seen from a comparison of Experiment 1 with Experiments 2 through 5 in Table 1 that a substantial increase in conversion is obtained if the calcination temperature is increased to 750° C to 1000° C as compared to a calcination temperature of 600° C.

While certain representative embodiments and details have been shown for the purpose of illustrating the invention, it will be apparent to those having skill in this art that various changes and modifications may be made therein without departing from the spirit or scope of the invention.

What is claimed is:

1. In the process of oxidative dehydrogenation of at least one hydrocarbon selected from the group consisting of butene-1, butene-2, 2-methyl-1-butene, 2-methyl-2-butene, 3-methyl-1-butene, n-pentene, 2,3-dimethyl-1-butene, 2,3-dimethyl-2-butene, 2-methyl-1-pentene, 2-methyl-2-pentene, 4-methyl-2-pentene, 3-methyl-1-pentene and 3-methyl-2-pentene, 2-ethyl-1-butene, under oxidative dehydrogenation conditions while in the presence of a catalyst consisting of cobalt-molybdate or cobalt-molybdate treated with potassium hydroxide in amounts from about 0.5 to about 2 percent by weight of the cobalt-molybdate in the presence of an oxidant in an amount to provide an oxygen/hydrocarbon mole ratio ranging from about 0.5/1 to about 5/1 at a temperature ranging from about 350° C to about 650° C and an LHSV of from about 0.5 to about 10, the improvement which comprises calcining the cobalt-molybdate or cobalt-molybdate treated with potassium hydroxide at temperatures between about 750° C and about 1100° C for at least one hour prior to use.

2. The method according to claim 1 in which the cobalt-molybdate is impregnated on a support.

3. The method according to claim 2 in which the support is alumina and the cobalt-molybdate is in amounts ranging from about 3 to about 50 weight percent based on the weight of the alumina.

4. The method according to claim 1 in which water is employed as a diluent.

5. The method according to claim 1 in which a mixture of 2,3-dimethyl-1-butene and 2,3-dimethyl-2-butene is employed in which about 65 to about 80 mole percent of the mixture comprises 2,3-dimethyl-2-butene.

6. The method according to claim 5 in which air is employed as the oxidant in amounts to provide an oxygen/hydrocarbon mole ratio of 0.5/1 to 5/1 and in which the cobalt-molybdate is impregnated on an alumina support in amounts ranging from about 10 to about 30 percent by weight of the alumina and in which water is employed as a diluent in amounts of 2/1 to 5/1 mole ratio of diluent/hydrocarbon.

7. In the process of oxidative dehydrogenation of at least one hydrocarbon selected from the group consisting of ethyl benzene and isopropyl benzene under oxidative dehydrogenation conditions while in the presence of a catalyst consisting of cobalt-molybdate or cobalt-molybdate treated with potassium hydroxide in amounts from about 0.5 to about 2 percent by weight of the cobalt-molybdate in the presence of an oxidant in an amount to provide an oxygen/hydrocarbon mole ratio ranging from about 0.5/1 to about 5/1 at a temperature ranging from about 350° C. to about 650° C. and an LHSV of from about 0.5 to about 10, the improvement which comprises calcining the cobalt-molybdate or cobalt-molybdate treated with potassium hydroxide at temperatures between about 750° C. and about 1100° C. for at least one hour prior to use.

8. The method according to claim 7 in which the cobalt molybdate is impregnated on an alumina support and the cobalt molybdate is in amounts ranging from about 3 to about 50 weight percent based on the weight of the alumina.

9. The method according to claim 7 in which water is employed as a diluent.

10. The method according to claim 7 in which air is employed as the oxidant in amounts to provide an oxygen/hydrocarbon mole ratio of 0.5/1 to 5/1 and in which the cobalt-molybdate is impregnated on an alumina support in amounts ranging from about 10 to about 30 percent by weight of the alumina and in which water is employed as a diluent in amounts of 3/1 to 5/1 mole ratio of diluent/hydrocarbon.

* * * * *